(12) United States Patent
Kruspe et al.

(10) Patent No.: US 6,984,980 B2
(45) Date of Patent: Jan. 10, 2006

(54) METHOD AND APPARATUS FOR NMR SENSOR WITH LOOP-GAP RESONATOR

(75) Inventors: Thomas Kruspe, Wienhausen (DE); Martin Blanz, Celle (DE); Peter Rottengatter, Isernhagen (DE)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/132,986

(22) Filed: Apr. 26, 2002

(65) Prior Publication Data
US 2003/0151408 A1    Aug. 14, 2003

Related U.S. Application Data

(60) Provisional application No. 60/356,695, filed on Feb. 14, 2002.

(51) Int. Cl.
   *G01V 3/00*   (2006.01)
(52) U.S. Cl. .................................................... 324/303
(58) Field of Classification Search ................ 324/303
   See application file for complete search history.

(56) References Cited

U.S. PATENT DOCUMENTS

| | | | |
|---|---|---|---|
| 4,350,955 A | * | 9/1982 | Jackson et al. ............. 324/303 |
| 4,435,680 A | | 3/1984 | Froncisz et al. ............ 324/316 |
| 4,446,429 A | | 5/1984 | Froncisz et al. ............ 324/316 |
| 4,480,239 A | | 10/1984 | Hyde et al. ................ 333/219 |
| 4,504,588 A | | 3/1985 | Gartner et al. ............. 502/24 |
| 4,504,788 A | | 3/1985 | Froncisz et al. ............ 324/316 |
| 4,623,835 A | | 11/1986 | Mehdizadeh et al. ...... 324/58.5 |
| 4,724,389 A | | 2/1988 | Hyde et al. ................ 324/318 |
| 4,734,647 A | * | 3/1988 | Yoshimura ................. 324/318 |
| 4,933,638 A | * | 6/1990 | Kleinberg et al. .......... 324/303 |
| 5,023,551 A | * | 6/1991 | Kleinberg et al. .......... 324/303 |
| 5,055,787 A | * | 10/1991 | Kleinberg et al. .......... 324/303 |
| 5,055,788 A | * | 10/1991 | Kleinberg et al. .......... 324/303 |
| 5,139,024 A | * | 8/1992 | Bryant et al. .............. 600/422 |
| 5,432,446 A | * | 7/1995 | MacInnis et al. ........... 324/303 |
| 5,629,266 A | * | 5/1997 | Lithgow et al. ............ 505/210 |
| 5,629,623 A | * | 5/1997 | Sezginer et al. ............ 324/303 |
| 5,644,231 A | * | 7/1997 | Wignall ..................... 324/303 |
| 5,744,957 A | * | 4/1998 | Vaughan, Jr. .............. 324/318 |
| 5,796,252 A | * | 8/1998 | Kleinberg et al. .......... 324/303 |
| 5,923,167 A | * | 7/1999 | Chang et al. .............. 324/303 |
| 6,026,560 A | * | 2/2000 | Wignall ..................... 29/607 |
| 6,163,151 A | * | 12/2000 | Wisler et al. .............. 324/303 |

(Continued)

FOREIGN PATENT DOCUMENTS

DE         3300767       7/1984

(Continued)

*Primary Examiner*—Brij Shrivastav
*Assistant Examiner*—Dixomara Vargas
(74) *Attorney, Agent, or Firm*—Madan, Mossman & Sriram, P.C.

(57) ABSTRACT

A loop-gap resonator for providing an excitation pulse in a down hole nuclear magnetic resonating (NMR) tool for determining a parameter of interest in a formation adjacent a borehole. The loop-gap resonator is constructed having one or more capacitive gaps formed in a nonmagnetic conductive loop. The loop-gap resonator may be deployed down a bore in a measurement while drilling (MWD) configuration or in a wire line configuration. The MWD configuration may utilize a non-rotating sleeve rotationally associated with the drill string.

29 Claims, 6 Drawing Sheets

U.S. PATENT DOCUMENTS

| | | | |
|---|---|---|---|
| 6,163,153 A | 12/2000 | Reiderman et al. | 324/314 |
| 6,255,817 B1 * | 7/2001 | Poitzsch et al. | 324/303 |
| 6,331,775 B1 * | 12/2001 | Thern et al. | 324/303 |
| 6,429,654 B1 * | 8/2002 | Itskovich et al. | 324/314 |
| 6,445,180 B1 * | 9/2002 | Reiderman et al. | 324/303 |
| 6,489,763 B1 * | 12/2002 | Goswami et al. | 324/303 |
| 6,492,809 B1 * | 12/2002 | Speier et al. | 324/303 |

FOREIGN PATENT DOCUMENTS

| | | |
|---|---|---|
| DE | 4003138 | 8/1990 |
| DE | 4138690 | 5/1993 |
| EP | 0445017 | 9/1991 |
| EP | 0560893 | 9/1993 |
| EP | 0581666 | 2/1994 |

* cited by examiner

METHOD AND APPARATUS FOR NMR SENSOR WITH LOOP-GAP RESONATOR

CROSS REFERENCE TO RELATED APPLICATIONS

The following application claims priority from U.S. Provisional Patent Application No. 60/356,695 entitled Method and Apparatus for NMR Sensor with Loop-Gap Resonator by Kruspe et al, which was filed on Feb. 14, 2002, which is hereby incorporated herein by reference in its entirety. This application is related to U.S. Pat. No. 6,163,153, by Reiderman et al, entitled Nuclear Magnetic Resonance Pulse Sequence for Optimizing Instrument Electrical Power Usage which is hereby incorporated herein by reference in its entirety.

BACKGROUND OF THE INVENTION

1. Field of the Invention

This invention relates to a NMR tool having a loop-gap resonator sensor for radio frequency generation and reception of NMR signals in zone of interest in a hydrocarbon bearing formation adjacent a borehole during measurement-while-drilling (MWD) or wire line operations down hole.

2. Description of the Related Art

To obtain hydrocarbons such as oil and gas, a drilling assembly (also referred to as the "bottom hole assembly" or the "BHA") carrying a drill bit at its bottom end is conveyed into the wellbore or borehole. The drilling assembly is usually conveyed into the wellbore by a coiled-tubing or a drill pipe. In the case of the coiled-tubing, the drill bit is rotated by a drilling motor or "mud motor" which provides rotational force when a drilling fluid is pumped from the surface into the coiled-tubing. In the case of the drill pipe, it is rotated by a power source (usually an electric motor) at the surface, which rotates the drill pipe and thus the drill bit.

Bottom hole assemblies ("BHA") generally include several formation evaluation sensors for determining various parameters of the formation surrounding the BHA during the drilling of the wellbore. Such sensors are usually referred to as the measurement-while-drilling ("MWD") sensors. Sensors are also deployed after the borehole drilling has been completed. Depending a sensory device down hole via a wire line performs such operations.

Such sensors, whether MWD or wire line, have traditionally utilized electro-magnetic propagation sensors for measuring the resistivity, dielectric constant, water saturation of the formation, and nuclear sensors for determining the porosity of the formation and acoustic sensors to determine the formation acoustic velocity and porosity. Other downhole sensors that have been used include sensors for determining the formation density and permeability. The bottom hole assemblies also include devices to determine the BHA inclination and azimuth, as well as pressure sensors, temperature sensors, gamma ray devices, and devices that aid in orienting the drill bit in a particular direction and to change the drilling direction. Acoustic and resistivity devices have been proposed for determining bed boundaries around and in some cases in front of the drill bit. More recently, nuclear magnetic resonance ("NMR") sensors have gained extreme interest as MWD sensors as well as wire line sensors as NMR sensors can provide direct measurement for water saturation porosity and indirect measurements for permeability and other formation parameters of interest.

NMR sensors utilize permanent magnets to generate a static magnetic field, $B_0$ in a formation surrounding the borehole in which the MWD or wire line tool is deployed. Typically a radio frequency (RF) solenoid coil is disposed between the permanent magnets or around the magnets to induce an RF magnetic field into the formation. The magnets and the RF coils are positioned so that the static magnetic field $B_0$ and the RF field occur perpendicular to each other in at least over a portion of the formation surrounding the borehole and the NMR tool. In this region of interest or region of investigation NMR measurements are made to determine the parameters of interest for the surrounding formation.

In MWD operations, NMR sensors can be located inside and outside of a drill collar for performing measurements on the formation and its fluid content. A conventional MWD drill collar comprises a metallic structure that conveys rotational torque required during drilling operations. Moreover, the drill collar provides a hollow center section that provides a conduit for the drilling fluid or drilling mud that is used to lubricate the drill bit and carry the drilled cuttings from the borehole to the surface. Since audio and radio frequency electromagnetic fields do not penetrate the metallic body of the drill collar, electromagnetic field sensors necessarily are mounted outside of the metallic drill collar body. Because these sensors are on the outside of the drilling collar, they are exposed to the abrasive rock in the formation during drilling operations and are thus subject to abrasion and wear resulting from particles in the drilling mud and the impact of the sensor against the earth formation during drilling.

In some cases, shields or protective coatings have been used on the drill collar in an attempt to protect these external sensors. Often, wear bands have been employed on the drill collar to provide an amount of standoff between the sensors and the formation, in an attempt to reduce or eliminate the abrasion of the earth formation rubbing against the sensor during drilling operations.

A typical MWD tool is described in EP-A-0581666 (Kleinberg). The MWD tool comprises a tubular drill collar, a drill head positioned at an axial end of the drill collar, and an NMR sensor. The NMR sensor comprises a pair of tubular main magnets, which generate a static ($B_0$) magnetic field, each of which is located in an internal recess of the drill collar. The Kleinberg tool provides an RF antenna located in an external recess in the drill collar between the main magnets. The RF antenna recess is optionally filled with a magnetically soft ferrite to improve the efficiency of the antenna.

A typical NMR well logging system is described in U.S. Pat. No. 4,629,986 (Clow et al.). In the Clow NMR tool, each of a pair of main permanent magnets is separated by a gap in which a solenoid RF antenna is symmetrically disposed. The symmetrical solenoid antenna has a core of high permeability ferromagnetic material (soft ferrite).

Known clown hole NMR tools use resonating antennas for radiating RF electromagnetic NMR pulses and/or receiving alternating magnetic fields at the resonance frequency of the detected NMR. Typically a NMR antenna is a simple solenoid coil in combination with an attached capacitor to form a resonating circuit. The high impedance of the typical NMR antenna raises the voltage amplitude in the typical antenna, thereby raising the risk of high-tension electric breakdowns due to arcing in the antenna and in the antenna connecting wires. The typical solenoid antenna is also subject to wear and deterioration or failure due to the abrasive effects of on the antenna from exposure to the formation during drilling operations. Thus, there is a need for a lower impedance antenna that lowers the antenna voltage and the associated risk of damage due to arcing. There is also a need for additional mechanical robustness than that offered by the typical resonating solenoid antenna that will improve the ruggedness of NMR tools and particularly the resonating element of the tool in the down hole environment.

SUMMARY OF THE INVENTION

The apparatus and method of the present invention overcome the disadvantages of the known down hole NMR tools. The present invention provides a bridged loop-gap resonator for transmission and reception of NMR signals in a down hole environment during either MWD or wire line operations. In one aspect of the present invention a NMR loop-gap resonator is presented comprising an elongated tubular structure with a longitudinal gap bridged by at least one capacitor. In another embodiment, a plurality of slots or gaps is formed in the loop-gap resonator to reduce voltage potential and inductance across the gap. The present invention provides a loop-gap resonator having relatively lower impedance than a typical solenoid antenna due to the low inductance of the single winding in the loop-gap resonator. The loop-gap resonator can be deployed in a MWD environment in a tool fixably attached to the drill string or rotationally attached to the drill string on a non-rotating sleeve surrounding the drill string. The present invention can also be deployed in a borehole via a wire line.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DETAILED DESCRIPTION OF A PREFERRED EMBODIMENT

The present invention provides several advantages over the solenoid antennas that have typically been used for NMR tools. The loop-gap resonator of the present invention provides a higher antenna Quality Factor "Q" due to the large cross sectional area of the loop-gap conductor. The loop-gap resonator of the present invention provides a higher degree of homogeneity than a solenoid coil antenna, as the flux lines do not escape loop-gap resonator except at the end of a resonator section. The loop-gap resonator of the present invention provides lower impedance than a typical NMR solenoid antenna, due to the low inductance of the equivalent single winding of the loop-gap resonator. The loop-gap resonator is also mechanically superior, more rugged and more robust than the typical NMR solenoid antenna.

The loop-gap resonator of the present invention exhibits lower parallel impedance. For transmission purposes, the lower parallel impedance of the loop-gap resonator provides a distinct advantage over a typical NMR solenoid coil. The lower impedance of the loop-gap resonator lowers the voltage amplitude requirement of the resonator, thereby reducing the risk of a high voltage electrical breakdown (arcing) in the resonator or the wires attached to the resonator.

During MWD operations, the NMR loop-gap resonator can be attached to a non-rotating sleeve, which is rotationally attached to a rotating drill string. The non-rotating sleeve can be fixably positioned in the well bore by extending pads or other extensible members from the non-rotating sleeve to the interior surface of the well bore. The pads fix the non-rotating sleeve and loop-gap resonator mounted therein, with respect to the well bore wall, while the drill string remains free to rotate and descend into the borehole. Alternatively, the loop-gap resonator NMR antenna may be attached to the rotating drill string during MWD operations or depended from a wire line into the borehole.

Figure 1:
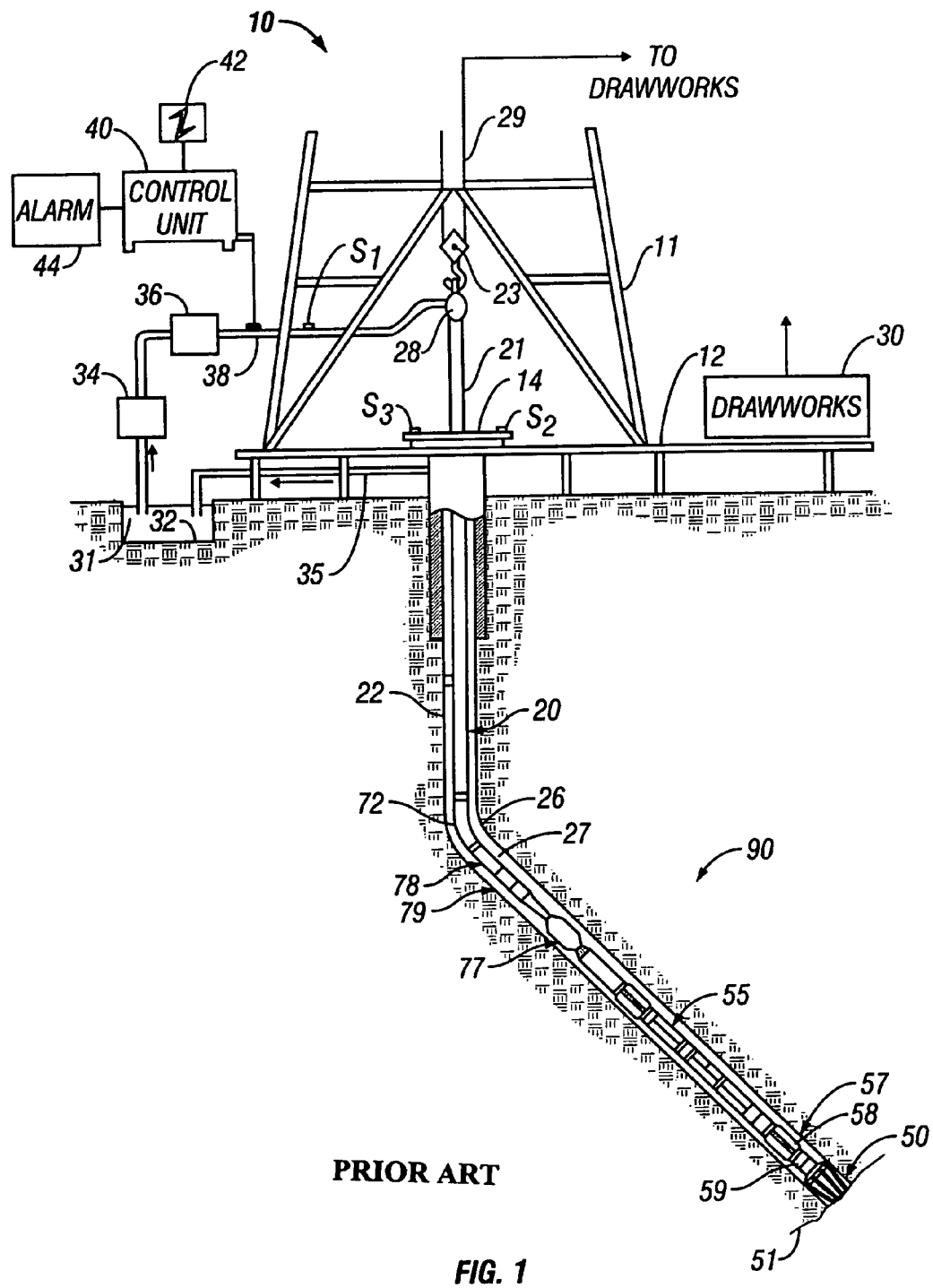
FIG. 1 illustrates a MWD drilling system with an NMR tool in accordance with the present invention in a well bore.

FIG. 1 illustrates a schematic diagram of a MWD drilling system 10 with a drill string 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28 and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger 36, fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ preferably placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In a preferred embodiment of the invention, rotating the drill pipe 22 only rotates the drill bit 50. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In the preferred embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

A drilling sensor module 59 is placed near the drill bit 50. The drilling sensor module contains sensors, circuitry and processing software and algorithms relating to the dynamic drilling parameters. Such parameters preferably include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an NMR tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$–$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 preferably includes a computer or a microprocessor-based processing system, memory for storing programs or models and data, a recorder for recording data, and other peripherals. The control unit 40 is preferably adapted to activate alarms 44 when certain unsafe or undesirable operating conditions occur.

Figure 2:
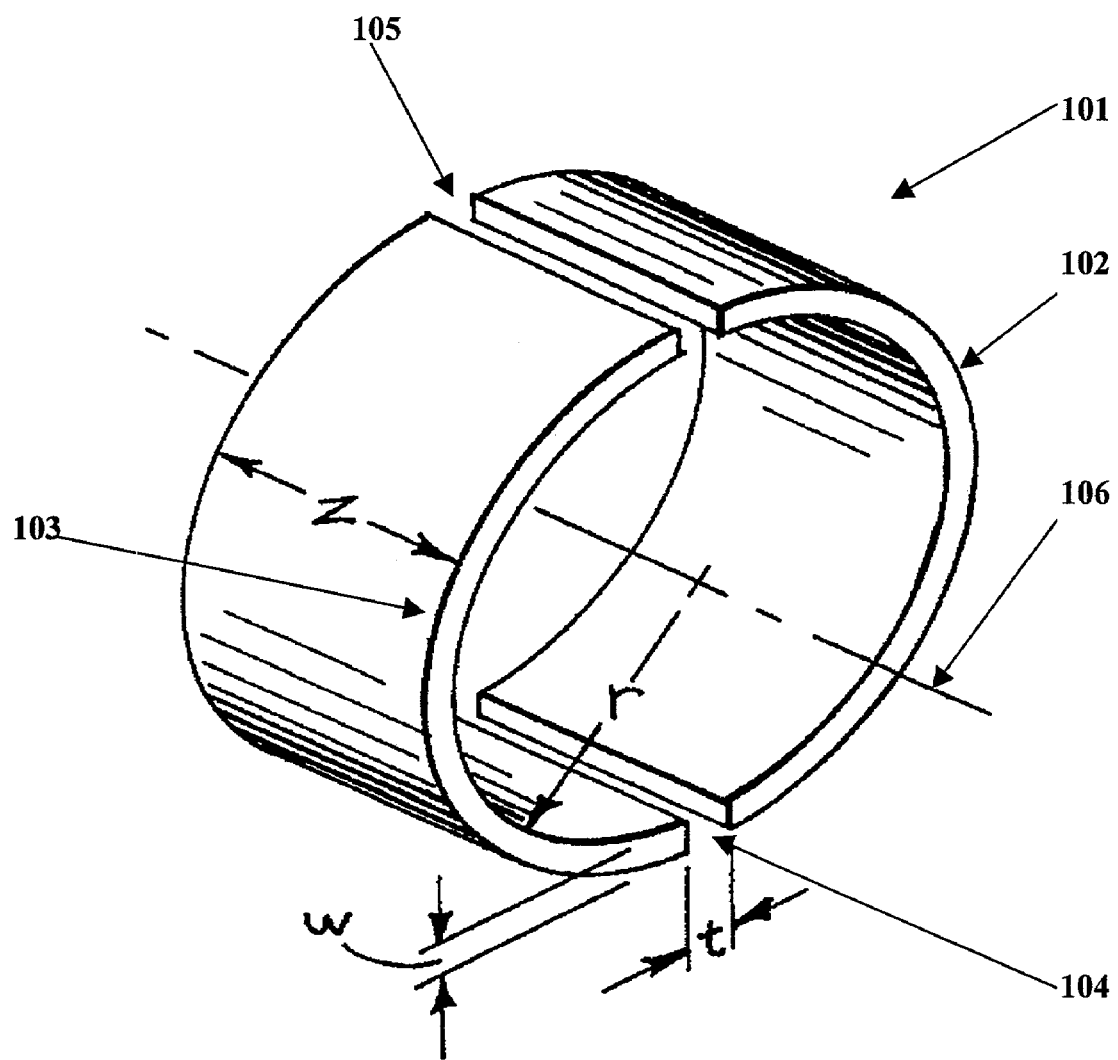
FIG. 2 is a perspective view of a loop-gap resonator employed in a preferred embodiment of the present invention.
Figure 2A:
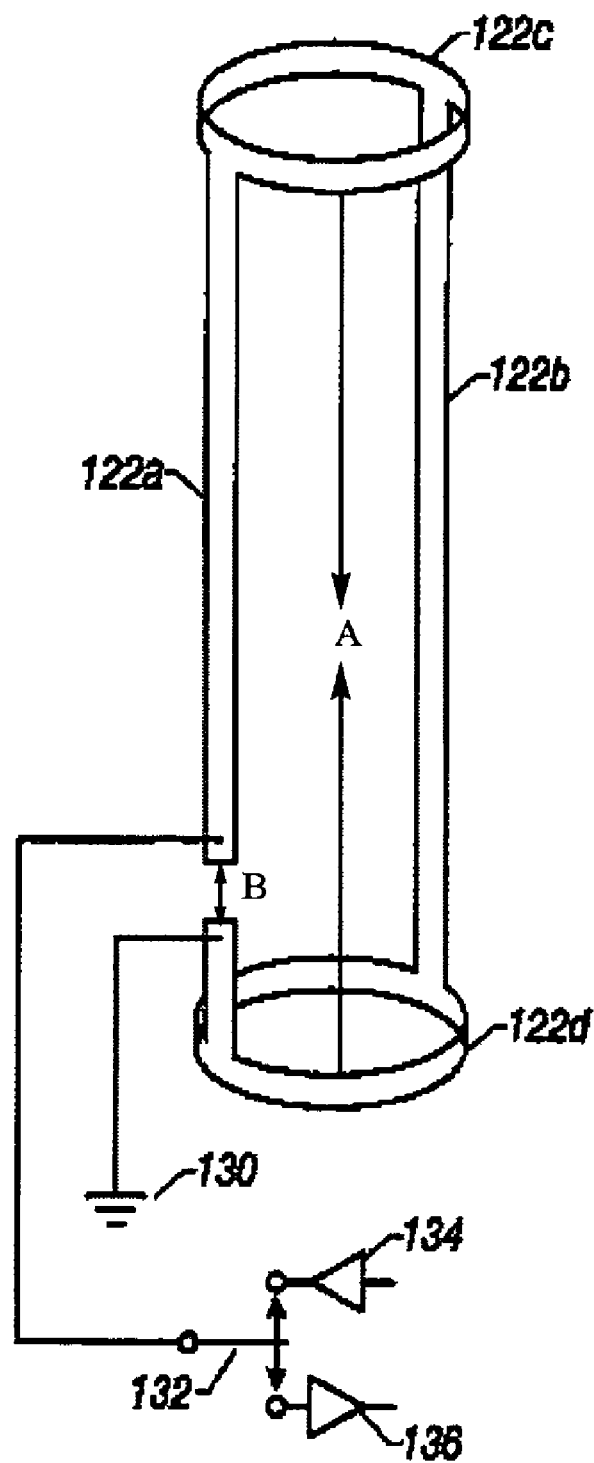

Turning now to FIG. 2, a loop-gap resonator 101 is illustrated. Referring particularly to FIG. 2 a loop gap resonator with two gaps is shown. The loop-gap resonator 101 employed in the present invention resonates at a radio frequency determined by its geometry. The loop-gap resonator 101 has dimensions, which are much less than the wavelength of the radio frequency signal at which it resonates. The capacitive and inductive elements are identifiable and the electromagnetic field oscillates between a magnetic field generated by the inductive element and an electric field generated by the capacitive element.

The inductive element in the resonator 101 is the loop, or ring, formed by two metallic pieces 102 and 103, and the capacitive element comprises the longitudinal gaps 104 and 105 formed at the juncture of the two pieces 102 and 103. The magnetic field produced by the resonator 101 is concentrated along a central axis 106, and the electric field is concentrated in the gaps 104 and 105. The magnetic flux flows through the opening defined by the loop and curves radial outward at each of its ends and along the outside of the loop to form a closed flux path. The resonant frequency of the resonator 101 is determined primarily by its geometry, and it can be constructed to operate over a wide range of frequencies of interest. Where the spacing (t) in the gaps 104 and 105 is much smaller than their width (w), the resonant frequency of a loop-gap resonator is as follows:

$$F = \frac{1}{2\pi}\left(\frac{1}{LC}\right)^{\frac{1}{2}} \quad (1)$$

where:

$$L = \frac{\mu \pi r^2}{z}$$

$$\frac{1}{C} = \sum_{m=1}^{n} \frac{t_m}{\in W_m z}$$

$\in$ = the dielectric constant of the material in the gaps;
$\mu$ = the permeability of free space;
n = the number of gaps, each having dimensions $t_m$ and $W_m$; and
z = the length of the resonator 101 in the direction of the central axis 106.

There are a number of characteristics of the loop-gap resonator, which are important when applying them to practical use. First, the length (z) has virtually no effect on the resonant frequency. Second, one or more gaps may be employed and these need not be of equal dimensions or provide equal capacitance. Multiple gaps in the loop-gap resonator reduce the voltage potential across each gap and reduce the intensity of the resulting electric fields. Increasing the length of the loop-gap resonator further enhances this intensity reduction effect. The additional gaps make the antenna more efficient as less current leakage occurs across the gaps.

The loop need not be circular although there are often advantages to a circular construction as will be described in more detail below. Since the drill string and drill collar are typically circular, a circular cross section for the loop-gap resonator facilitates mechanical compatibility between the drill assembly and the loop-gap resonator. And finally, energy may be applied or removed from the loop-gap resonator in either of two ways. Energy is inductively coupled to or from the resonator by a conductive loop, which encircles magnetic flux flowing through the loop, which is connected to the end of a transmission line. Alternatively, energy can be coupled capacitively or galvanically to and from the loop-gap resonator by connecting the transmission line to the plates of one of the loop-gap resonator's capacitive elements through an impedance matching network. In a preferred embodiment, the gaps 104 and 105 of the loop-gap resonator are filled with dielectric material or capacitors, which determine the resonant frequency for the loop-gap resonator.

In a preferred embodiment, the loop and capacitive element comprising the resonate circuit are excited by an RF signal. The preferred RF signal comprises a modulated RF signal, and in particular a modified CPMG sequence as described in the Reiderman patent, U.S. Pat. No. 6,163,153.

The loop-gap resonator cylinder can comprise the external surface of the NMR sensor, whether mounted on a rotational drilling collar, the drill string or a wire line. The loop-gap resonator, as the external surface in each of these configurations is in contact with the conductive drilling mud filling the borehole. In one embodiment of the present invention, the loop-gap resonator surface exposed to the drilling mud is covered with an insulating material to off set the effects of contact with the conductive drilling mud. One embodiment provides the said insulating material in the neighborhood of the gap only. The loop-gap resonator is of rugged construction, which protects the sensitive portion of the NMR sensor. The gaps 104 and 105 are filled with dielectric material, which provide capacitance for the resonant circuit. An additional layer of insulation material may cover the loop-gap resonator cylinder exterior surface to insulate the loop-gap resonator cylinder from the conductive drilling mud.

Multiple gaps can be provided to reduce the voltage potential generated across each individual gap in the loop-gap resonator. The gaps are preferably bridged with capacitors, but can be provided and utilized without a bridged insulation or dielectric material. The loop-gap resonator is the theoretical equivalent of a single turn solenoid with a capacitor in the gap. Known down hole NMR tools utilize a solenoid antenna and capacitor bank provided in the electronic circuitry to form a resonate circuit. In a preferred embodiment, the capacitive element for the loop-gap resonator is provided as an insulation element inserted into the gaps of the loop-gap resonator. In an alternative embodiment a capacitor is provided in the electronic circuitry attached to the gap in the loop-gap resonator via a cable. A preferred embodiment provides the capacitor in the gap configuration, which is more efficient due to the high currents that would flow into the cables going to, the capacitor in the alternative embodiment of the resonant circuit. The cables form additional inductance and ohmic resistance and thus store energy and cause power loss thereby reducing the efficiency of the resonant circuit.

In a preferred embodiment, the loop-gap resonator both transmits NMR excitation pulses and receives NMR signals from the zone of interest. The loop-gap resonator is multiplexed between receive and transmit electronics in the preferred embodiment. In a preferred embodiment, a loop-gap resonator with a single gap provides an equivalent to a single turn coil, however, a plurality of gaps can be provided to reduce the voltage across each individual gap. A loop-gap resonator with two or more gaps can be utilized. Due to the reduced self inductance of the formed fractional loops, the voltages at the gaps are lower than with a single gap, while keeping the current through the loops the same.

While a preferred embodiment is shown having a longitudinal inductive element with an air gap, which can be filled with an insulator or capacitor, any inductive element shape can be utilized which can be made to resonate. Moreover, the gap may be a void as an air gap or simply a discontinuity in the inductive element, that is, a section in the inductive element having an electrical property other than that exhibited by the inductive element.

As discussed above, the conductive drilling mud poses a design consideration in the loop-gap resonator configuration. The exterior surface of the loop-gap resonator contacts the conductive drilling mud which presents the potential of short circuiting the loop-gap resonator sections by allowing current to flow in the conductive mud between the loop-gap resonator sections. In the extreme case, an insulating material is placed on the external surface of the loop-gap resonator to keep the conductive mud from contact the loop-gap resonator to eliminate or substantially reduce shorting or arc across the gaps between the loop-gap resonator elements.

The preferred loop-gap resonator configuration generates a highly homogeneous field inside and to a lesser degree also outside. The homogeneity is due to the physics of the loop-gap resonator. The magnetic flux lines cannot escape from the loop-gap resonator until the magnetic flux exits one end of the loop-gap resonator, passes through the formation and enters the other end of the loop-gap resonator. This is not the case in the typical solenoid NMR antenna having a plurality of turns in which flux ordinarily escapes from and into the gaps between the windings of the solenoid. The loop-gap resonator, however, comprises a solid metal longitudinal member, typically a sleeve or cylinder, so that the flux cannot escape though the longitudinal member.

An NMR sensor antenna comprising a loop gap resonator with its symmetry axis collinear with the borehole axis is also advantageous in combination with a static bipolar magnet configuration where the static magnetic field lies in a plane orthogonal to the drill string [e.g. NUMAR's wireline NMR tools].

Figure 3:
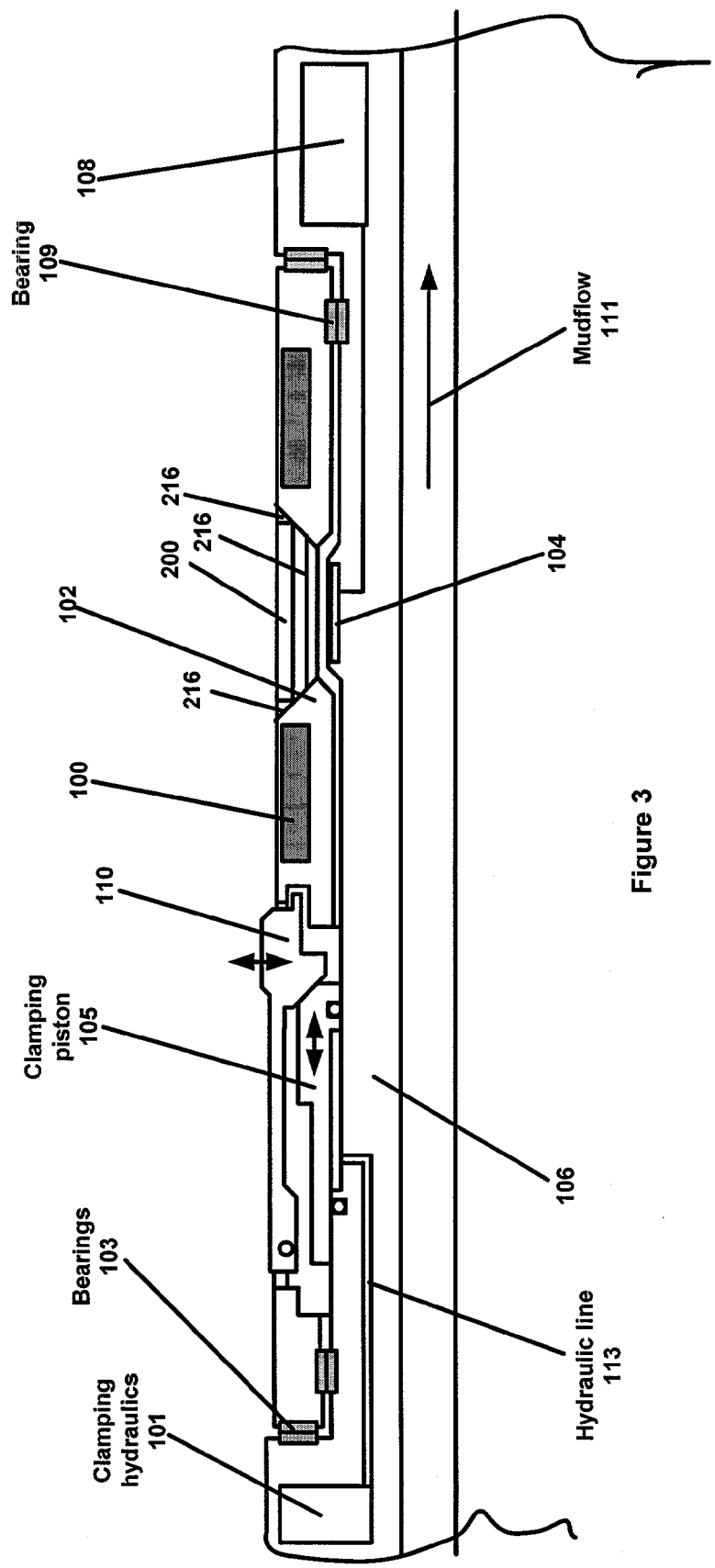
FIG. 3 is a partial cross-section of a MWD NMR tool with an antenna comprising a bridged loop-gap resonator in accordance with one embodiment of the present invention.

Turning now to FIG. 3, a side view of a schematic representation of the present invention installed on a MWD NMR tool configuration having a non-rotating sleeve. A layer of ferrite 216 or other flux guiding material is provided underneath the loop-gap resonator cylinder to guide the magnetic flux along the flux guiding material and keep it away from the conductive surface of the non-rotating sleeve 102. In a preferred embodiment, the flux guiding material comprises a powdered iron mixed with epoxy bonded together to form a soft magnetic material. This soft magnetic material provides flux-guiding and magnetic properties that are superior to ferrite. In addition, other materials such as thin ferromagnetic metal or metal sheets or amorphous metal can be used as a flux guiding material. The flux guiding material inside the loop gap resonator diminishes losses due to high frequency eddy currents and reduces stored magnetic energy.

As shown in FIG. 3, NMR loop-gap resonator 200 attached to a non-rotating sleeve on a rotating drilling collar is shown. The NMR tool comprises permanent magnets 100 and loop-gap resonator mounted on the non-rotating sleeve 102 in accordance with one embodiment of the present invention. As shown in FIG. 3, non-rotating sleeve 102 houses permanent magnets 100 and clamping rib 110. Clamping rib 110 rotationally fixes permanent magnets 100 and non-rotating sleeve 102 relative to the formation when pushed out by a clamping piston 105 while the drill string 106 collar is free to rotate. The clamping piston is activated and retracted by clamping hydraulics according to the timing of the measurement. Fixation of magnets 100 and non-rotating sleeve 102 with respect to the well bore and adjacent formation effectively decouples the non-rotating sleeve 102 and magnets 100 from laterally movement of drill collar 106 and forces the NMR-sensor to a rest during drilling operations. Bearings 103 and shock absorbers such as rubber blocks are implemented to effectively decouple the non-rotating sleeve. The loop-gap resonator 200 and tuning and adapter electronics 108 are provided on the non-rotating sleeve 102.

As shown in FIG. 3, permanent magnets 100 are located in non-rotating sleeve 102, which also functions as the NMR MWD tool body. The non-rotating sleeve/tool body 102 is constructed of steel or some other material that is highly conductive and nonmagnetic. The non-conducting flux guide 216 separates non-rotating sleeve/tool body 102 from loop-gap resonator 200.

Figure 4:
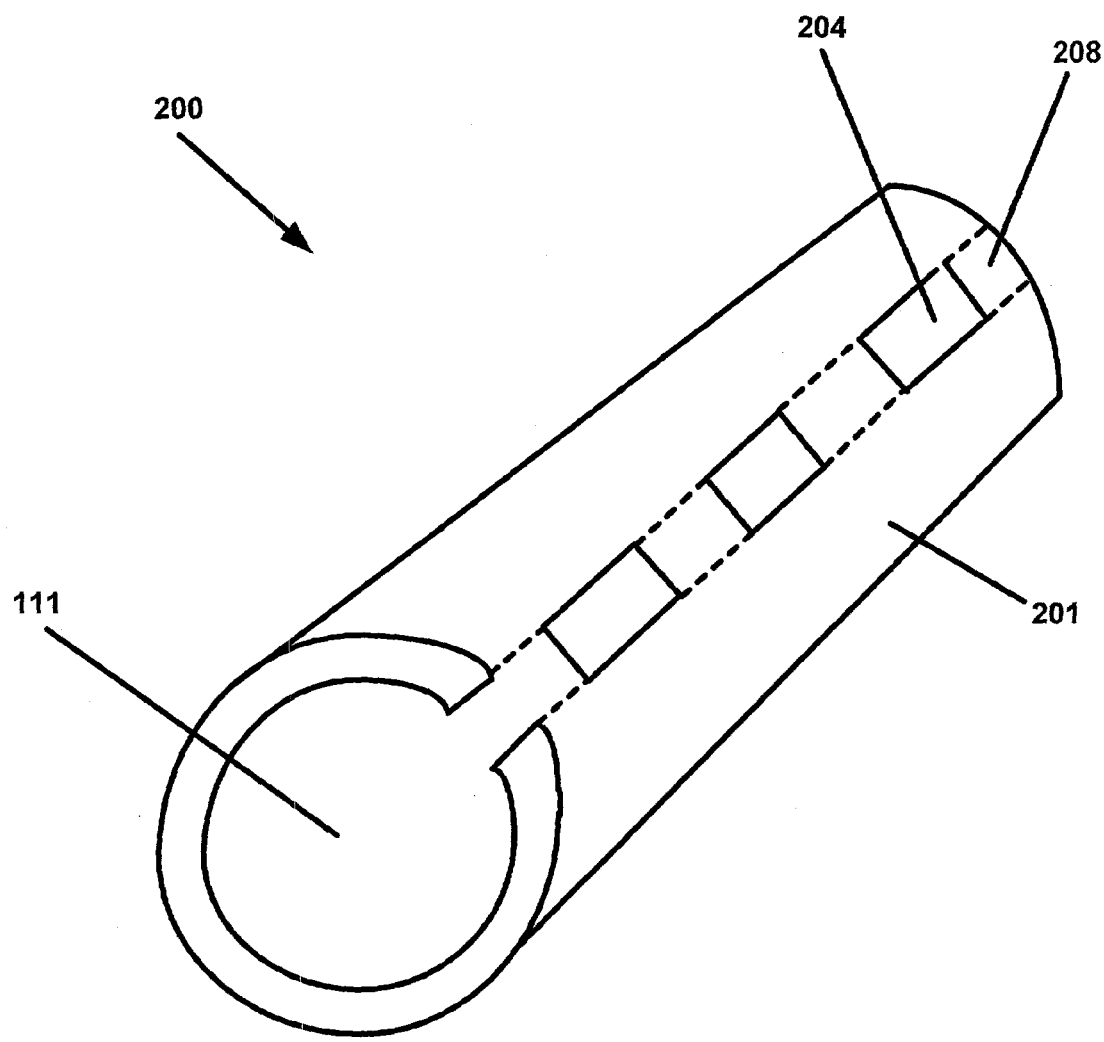
FIG. 4 is a three-dimensional illustration of a preferred embodiment of the loop-gap resonator provided by the present invention.
Figure 5:
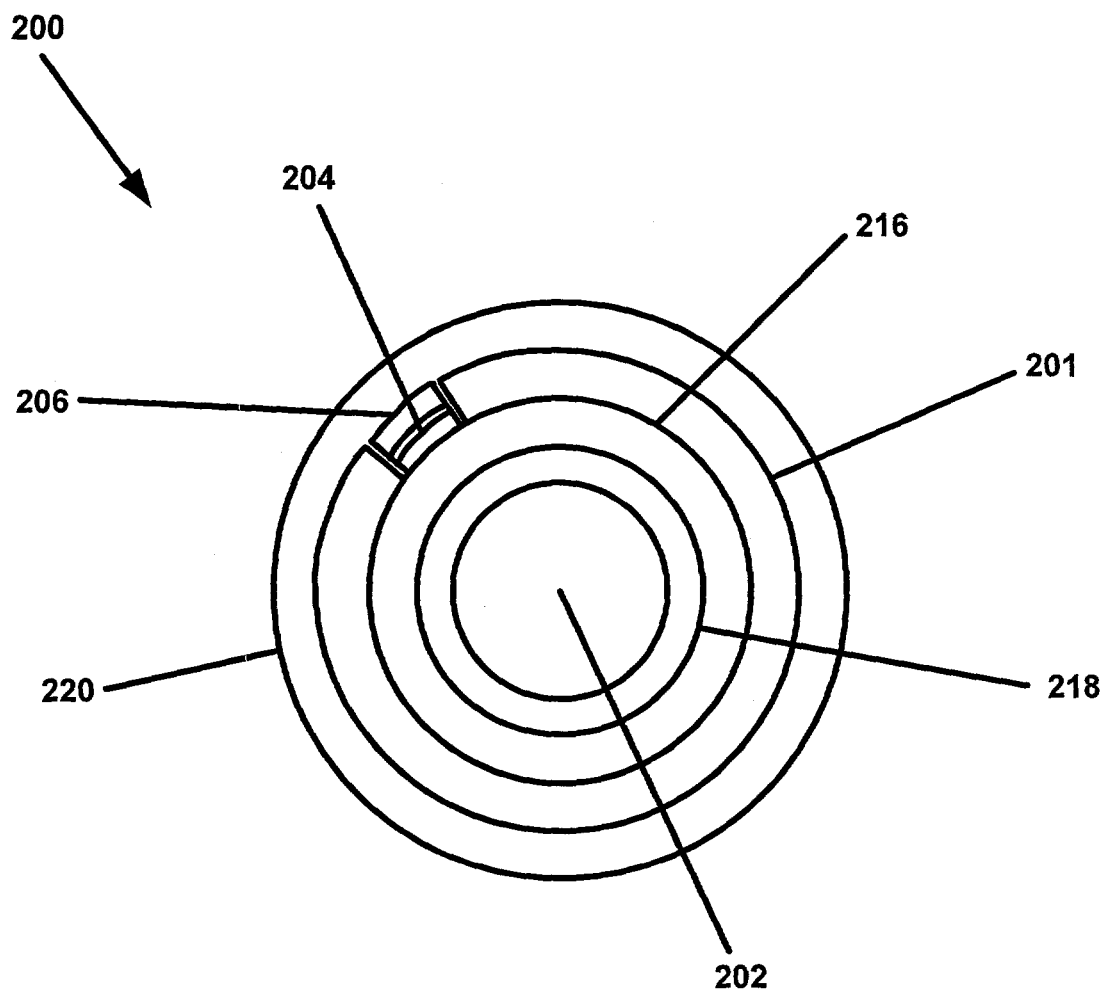
FIG. 5 is a cross section of a MWD NMR tool and bridged loop-gap resonator of FIG. 3

Turning now to FIG. 4, a three-dimensional view of a preferred loop-gap resonator is illustrated. As shown in FIG. 4, the preferred loop-gap resonator 200 is constructed of a loop 201 of conductive material having at least one capacitive slot 208 formed in the loop 201 so that the tubular form of the loop 201 is interrupted along the entire length of the loop by the slot 208. Slot 208 is bridged by at least one and preferably a plurality of capacitors 204 aligned along slot 208. A current is run through the wires 214 to capacitors 204 to cause loop 201 to resonate. In a preferred embodiment the electrically conductive loop 201 of loop-gap resonator 200 is covered with a non-conductive insulation material 220, to insulate the loop-gap resonator from the electrically conductive drilling mud as shown in FIG. 5. This insulation prevents the electrically conductive mud from bridging the loop-gap resonator, which would effectively short-circuit it.

Turning now to FIG. 5, a cross section of a preferred embodiment of the loop-gap resonator 200 of the present invention is illustrated. A non-conductive spacer 206 is formed over capacitor 204. An electrically non-conducting softmagnetic material 216 separates conductive loop-gap resonator 201 from the tool body 218. A layer of insulation 220 is optionally provided to insulate the loop gap resonator from conductive drilling mud present in the well bore. A center void 202 is formed in the center of the tool for drilling mud to pass through in a MWD configuration and for electronics to be encapsulated in a wire line configuration.

While preferred embodiments have been shown and described, various modifications and substitutions may be made thereto without departing from the spirit and scope of the invention. Accordingly it is to be understood that the present invention has been described by way of illustrations and not limitations.

What is claimed is:

1. A downhole nuclear magnetic resonance (NMR) tool, comprising:
   a loop gap resonator surrounding a body of the downhole tool for at least one of:
   transmitting an RF magnetic field into a formation and receiving a signal from the formation, the resonator comprising a tubular structure, the tubular structure having a longitudinal axis aligned with a longitudinal axis of the downhole tool body; and
   a plurality of variable length gaps formed along a longitudinal length of the resonator wherein the gaps forms a continuous separation of the tubular structure wherein the gaps form at least two separations having different widths.

2. The downhole tool of claim 1, further comprising:
   at least one capacitor for bridging at least one of the plurality gaps.

3. The downhole cool of claim 2, wherein the capacitor comprises:
   a variable capacitor, such that the variable capacitor can be adjusted to alter a resonant frequency of the resonator.

4. The downhole tool of claim 1 wherein the resonator is made of a conductive nonmagnetic material.

5. The downhole tool of claim 1, further comprising:
   a nonconductive insulator material covering a surface of the resonator to insulate the resonator from conductive fluid.

6. The downhole tool of claim 1, further comprising:
   a pair of electrically insulated wires connecting a capacitor between opposing edges of at least one of the gaps.

7. The downhole tool of claim 1 further comprising:
   a coupler coil connected across a transmission line and mounted adjacent the resonator to produce a signal on the transmission line which is responsive to nuclear magnetic resonance spin echo signals produced in a region of interest.

8. The downhole tool of claim 1, further comprising:
   a coupling positioned adjacent the resonator for coupling signals detected by the resonator to receiving electronics.

9. The downhole tool of claim 1, further comprising:
   a soft magnetic, flux-guiding material positioned inside the resonator.

10. The downhole tool of claim 1, wherein a signal for generating the RF magnetic field in the formation, further comprises RF modulation.

11. The downhole tool of claim 10, wherein the signal further comprises a modified CPMG sequence.

12. A method for measuring a parameter of interest of a formation, comprising:
    exciting a loop gap resonator with an RF signal, the resonator surrounding a nuclear magnetic resonance (NMR) tool body, the resonator having a tubular structure and a plurality of variable length gaps, wherein the gaps forms at least two continuous separations of the tubular structure having different widths, for at least one the set consisting of: transmitting an RF magnetic field into a region of interest in the formation and receiving a NMR signal from the formation.

13. The method of claim 12, further comprising:
    bridging at least one of the gaps with one or more capacitors.

14. The method of claim 13, wherein the capacitor comprises a variable capacitor, such that the variable capacitor can be adjusted to alter a resonant frequency of the resonator.

15. The method of claim 12 wherein the resonator is made of a conductive nonmagnetic material.

16. The method of claim 12, further comprising:
    covering a surface of the resonator with a nonconductive insulator to insulate the resonator from conductive fluid.

17. The method of claim 12, further comprising:
    connecting a capacitor between the longitudinal edges with a pair of electrically insulated wires.

18. The method of claim 12, further comprising:
    connecting a coupler coil across a transmission line and adjacent the resonator to produce a signal on the transmission line, which is responsive to nuclear magnetic resonance spin echo signals, produced in a region of interest.

19. The method of claim 12, further comprising:
    guiding flux in a soft magnetic, flux-guiding material inside the resonator.

20. The method of claim 12, further comprising:
    coupling signals detected by the resonator to receiving electronics.

21. The method of claim 12, wherein the RF signal, further comprises RF modulation.

22. The method of claim 21, wherein a signal for generating an RF pulse in the region of interest in the formation further comprises a modified CPMG sequence.

23. An apparatus comprising:
a loop gap resonator surrounding a body of a downhole nuclear magnetic resonance tool, the resonator comprising a tubular structure having a longitudinal axis aligned with a longitudinal axis of the tool body, wherein the tubular structure is interspersed by a plurality of variable length continuous gaps along an entire longitudinal length of the tubular structure, wherein the gap forms at least two continuous separations of the tubular structure having different widths; and
at least one capacitor which bridges at least one of the gaps.

24. The apparatus of claim 23, further comprising:
a pair of electrically insulated wires which connect a capacitor between the longitudinal edges.

25. The apparatus of claim 23, wherein the capacitor comprises a variable capacitor connected, such that the variable capacitor can be adjusted to alter the resonant frequency of the resonator.

26. A method for measuring a parameter of interest for a formation, comprising:
exciting a loop gap resonator surrounding a nuclear magnetic resonance tool body with an RF signal, the resonator having a tubular structure interspersed by a a plurality of variable length gaps forming at least two continuous separations of the tubular structure having different widths, for at least one the set consisting of:
transmitting an RF magnetic field into a formation and receiving a signal from the formation; and
bridging at least one of the gaps with one or more capacitors.

27. A method for measuring a parameter of interest for a formation, comprising:
exciting a loop gap resonator surrounding a nuclear magnetic resonance tool body with an RF signal resonator having a tubular structure having a plurality of longitudinal edges interspersed by a plurality of variable length longitudinal gaps wherein the at least two of the gaps form continuous separations different widths in the tubular structure, for at least one of: transmitting an RF magnetic
field into a formation and receiving a signal from the formation.

28. The method of claim 27, further comprising:
connecting a capacitor between the longitudinal edges with a pair of electrically insulated wires.

29. The method of claim 27, wherein the capacitor comprises a variable capacitor across the wires, such that the variable capacitor can be adjusted to alter a resonant frequency of the resonator.

* * * * *